(12) United States Patent
Castillo et al.

(10) Patent No.: US 11,853,659 B2
(45) Date of Patent: Dec. 26, 2023

(54) PROCEDURAL MODEL OF FIBER AND YARN DEFORMATION

(71) Applicant: SEDDI, INC., New York, NY (US)

(72) Inventors: Carlos Castillo, Madrid (ES); Miguel A. Otaduy, Madrid (ES); Carlos Aliaga, Madrid (ES); Jorge Lopez, Madrid (ES)

(73) Assignee: SEDDI, INC., New York, NY (US)

( * ) Notice: Subject to any disclaimer, the term of this patent is extended or adjusted under 35 U.S.C. 154(b) by 289 days.

(21) Appl. No.: 17/307,523

(22) Filed: May 4, 2021

(65) Prior Publication Data

US 2021/0256172 A1  Aug. 19, 2021

Related U.S. Application Data

(63) Continuation of application No. PCT/US2019/060024, filed on Nov. 6, 2019.

(60) Provisional application No. 62/760,538, filed on Nov. 13, 2018.

(51) Int. Cl.
*G06F 30/20* (2020.01)
*G06F 113/12* (2020.01)
*D02G 3/00* (2006.01)
*G06T 19/00* (2011.01)
*G01N 33/36* (2006.01)

(52) U.S. Cl.
CPC .............. *G06F 30/20* (2020.01); *G06T 19/00* (2013.01); *D02G 3/00* (2013.01); *G06F 2113/12* (2020.01); *G06T 2210/16* (2013.01)

(58) Field of Classification Search
CPC ...... G06F 30/20; G06F 2113/12; G06T 19/00; G06T 2210/16; D02G 3/00; G01N 33/365
See application file for complete search history.

(56) References Cited

U.S. PATENT DOCUMENTS

| | | | |
|---|---|---|---|
| 8,170,842 B2 * | 5/2012 | Ognjanovic | G06F 30/23 703/2 |
| 10,410,380 B2 * | 9/2019 | Bala | G06T 15/00 |
| 11,003,810 B2 * | 5/2021 | Fukuda | G06F 30/20 |

OTHER PUBLICATIONS

Peng, X., et al. "A simple anisotropic hyperelastic constitutive model for textile fabrics with application to forming simulation" Composites: Part B, vol. 52, pp. 275-281 (2013) (Year: 2013).*

(Continued)

*Primary Examiner* — Jay Hann
(74) *Attorney, Agent, or Firm* — Marton Ribera Schumann & Chang LLP; Chien-Ju Alice Chuang; Hector J. Ribera

(57) ABSTRACT

Modeling cross-sections of yarn may include receiving yarn simulation input comprising a descriptive model of a general curvature followed by the yarn, providing a plurality of fibers distributed radially from the center of a ply, setting a base position based on parameters, applying a strain model to simulate the effect of stretch forces applied to the yarn, and outputting a yarn model indicating position and directionality of fibers in the yarn. The technology also relates to real-time modeling of a garment comprising a fabric. For instance, real-time modeling of a garment may include providing an input associated with one or more parameters of the fabric, receiving frames of a computer simulated garment, the computer simulated garment including a simulation of the fabric, the fabric simulation including yarns simulated based on a yarn model.

15 Claims, 3 Drawing Sheets

(56) References Cited

OTHER PUBLICATIONS

Hu, X., et al. "Review of Cloth Modeling" IEEE Int'l Colloquium on Computing Communication Control & Management, pp. 338-341 (2009) (Year: 2009).*
Cirio, G., et al. "Yarn-Level Simulation of Woven Cloth" ACM Transactions on Graphics, vol. 33, No. 6, article 207 (2014) (Year: 2014).*
Khungurn et al., "Matching Real Fabrics with Micro-Appearance Models", ACM Transactions on Graphics, 2015, pp. 1-25.
Sadeghi et al., "A Practical Microcylinder Appearance Model for Cloth Rendering", ACM Transactions on Graphics, vol. 32, No. 2, Article 14, 2013, pp. 1-12.
Zhao et al., "Fitting Procedural Yarn Models for Realistic Cloth Rendering", SIGGRAPH 2016 Proceedings, pp. 1-11.

\* cited by examiner

PROCEDURAL MODEL OF FIBER AND YARN DEFORMATION

CROSS-REFERENCE TO RELATED APPLICATIONS

This application is a continuation of International Application No. PCT/US2019/060024 titled "Procedural model of fiber and yarn deformation," filed Nov. 6, 2019, which claims priority to U.S. Provisional Patent Application No. 62/760,538 entitled "Procedural model of fiber and yarn deformation," filed Nov. 13, 2018, all of which are incorporated herein by reference in its entirety.

BACKGROUND

This disclosure generally relates to computer modeling systems, and more specifically to a system and method for procedural modeling of fiber and yarn deformation in computer graphics applications.

In computer graphic applications, the accurate and lifelike modeling of clothing and other items made of fabric has been a long-standing goal, and a key component for realistic animations in video games, films, and other computer-modeling applications. Fabrics were traditionally modeled as two-dimensional sheets of very thin composition. Models for simulation of different fabrics typically focused on the appearance of the surface or surfaces of the two-dimensional sheet model. However, these models lacked detail and realism, particularly when examining up close or in scenes or other vignettes where the fabric was displayed close to the viewer. For example, in avatar-based online shopping applications, an avatar models items of clothing for a consumer who is trying to make a purchase decision. In such applications, the detail and realistic appearance of the clothing is critical. A sweater made of thick wool yarn cannot be accurately modeled in the surface of a two-dimensional sheet. With the recognition of these shortcomings, more recently, new approaches have developed for the modeling of cloth or fabrics.

Cloth is made of yarns that are stitched together forming semi-regular patterns. The macroscopic behavior and look of the cloth is dictated by the yarns and the interaction between the yarns. The overall appearance of fabrics is the result of the aggregate effects of its smallest building blocks. Namely, the radiance reaching the camera sensor after the light interacts with each microscopic fiber. Thus, fiber-based models are needed, not only for rendering photorealistic fabric at close-up distances, but also to accurately match the appearance of garments in order to create believable virtual replicas. In these models, each yarn or even the fibers making up the plies in a yarn, is modeled to reach the required microscopic-level. However, modeling at the scale of fibers implies very high requirements in terms of resources, especially in memory storage, also affecting scene's load. To address these problems, procedural modeling approaches have been proposed to alleviate the memory storage requirements and speed-up the scene generation, allowing real-time on-the-fly modeling of fabrics at the fiber level in an efficient pipeline that can be used in a wide range of computer graphics applications, like video games, animated films, virtual or augmented reality applications, garment design, garment fitting, and the like.

Procedural modeling has been used in computer graphics to create fabric models minimizing the user manual intervention. Instead of handcraft 3D models and store them, algorithms and rules are used to control a set of parameters of statistical models of fiber bundles, plies, yarns and structural patterns (e.g.: woven, knit . . . ). For example, Zhao et al. (2016), in their paper titled "Fitting Procedural Yarn Models for Realistic Cloth Rendering," describe "an automatic fitting approach to create high-quality procedural yarn models of fabrics with fiber-level details." As explained in their paper, they fit data from computed tomography ("CT") scans to procedural models in order to automatically recover parameters of the fibers, like twisting and hairiness, and augment the models with a measurement-based model of flyaway fibers. However, this model still requires the fitting and express insertion of migration and flyaway fibers arbitrarily. Moreover, this prior approach does not allow for modeling of the enhanced fibers under different strain circumstances or model the effect of yarn strain on the distribution and appearance of flyaway fibers the way a textile would naturally do.

Thus, what is needed, is a programmatic approach to modeling more realistic fabrics by introducing fiber migration and fly-out consistent with a more realistic and natural behavior of real fabrics and that allows for modeling the fibers under different strain conditions.

BRIEF SUMMARY

According to various embodiments of the present invention, a yarn modeling approach is provided.

In one embodiment, a method for generating fiber curves for a yarn simulation is provided. Input parameters are received, for example from a user or optical capture, and applied to a yarn simulation curve to define a yarn model. In one embodiment, the yarn model includes parametrically generated fiber plies, including fiber migration and fly-out. In one embodiment, pseudo-random functions define the frequency of fiber migration and fly-out. The locations of fibers are programmatically generated based on random functions. The amount of fiber fly-out is determined based on the distance to the fiber endings. In one embodiment, the yarn model is augmented with the application of a strain model on a cross-sectional basis. The strain model computes the strained shift and twist of each fiber in the yarn for each cross-sectional segment. A tangential directional vector resulting from the yarn strain provides the direction of each fiber in the yarn at each location. The yarn model is used to provide a modeled yarn output that may be used in a fabric simulation. For example, in one embodiment, the procedural yarn model is voxelized and stored in a 3D grid for use in producing final images according to the model. According to one embodiment, the occupation of each cube or voxel is determined and stored in a voxel grid.

The figures depict various example embodiments of the present disclosure for purposes of illustration only. One of ordinary skill in the art will readily recognize form the following discussion that other example embodiments based on alternative structures and methods may be implemented without departing from the principles of this disclosure and which are encompassed within the scope of this disclosure.

DETAILED DESCRIPTION

The above and other needs are met by the disclosed methods, a non-transitory computer-readable storage medium storing executable code, and systems for 3D modeling of clothing and cloth items in computer applications, including, for example, garment design and virtual modeling, motion capture applications, biomechanics and ergonomics design and simulation, education, business, virtual and augmented reality shopping, and entertainment applications, including animation and computer graphics for digital movies, interactive gaming and videos, human, animal, or character simulations, virtual and augmented reality applications, robotics, and the like.

The Figures and the following description describe certain embodiments by way of illustration only. One of ordinary skill in the art will readily recognize from the following description that alternative embodiments of the structures and methods illustrated herein may be employed without departing from the principles described herein. Reference will now be made in detail to several embodiments, examples of which are illustrated in the accompanying figures.

The systems and methods according to the various embodiments described a procedural approach to modeling yarn in order to replicate real yarns. According to one embodiment, yarn parameters are fitted to a simulated yarn curve definition to define a cross-section of a modeled yarn. A cross section is a group of plies that contain fibers. The fibers are distributed from the center of each ply radially. The end position of a fiber is defined by two parameters: a two-dimensional position calculated with a uniform random function and a distance from the center of the fiber to the center of the ply calculated with a random function according to a distribution function, for example, in one embodiment, a Cauchy distribution. Different distribution functions may be used in different embodiments. Fiber migration and fly-out effects are also parametrically modeled for each fiber based on probability distribution functions. The yarn model is further augmented with a strain input to simulate the effect of stretch forces applied to the yarn. The effect of the stretch results in twist and directional changes to fibers that are simulated according to embodiments of the invention to provide a realistic simulation of the yarn. According to another embodiment, the simulation may be output by voxelizing the 3-dimensional yarn model for rendering as an image.

Figure 1:
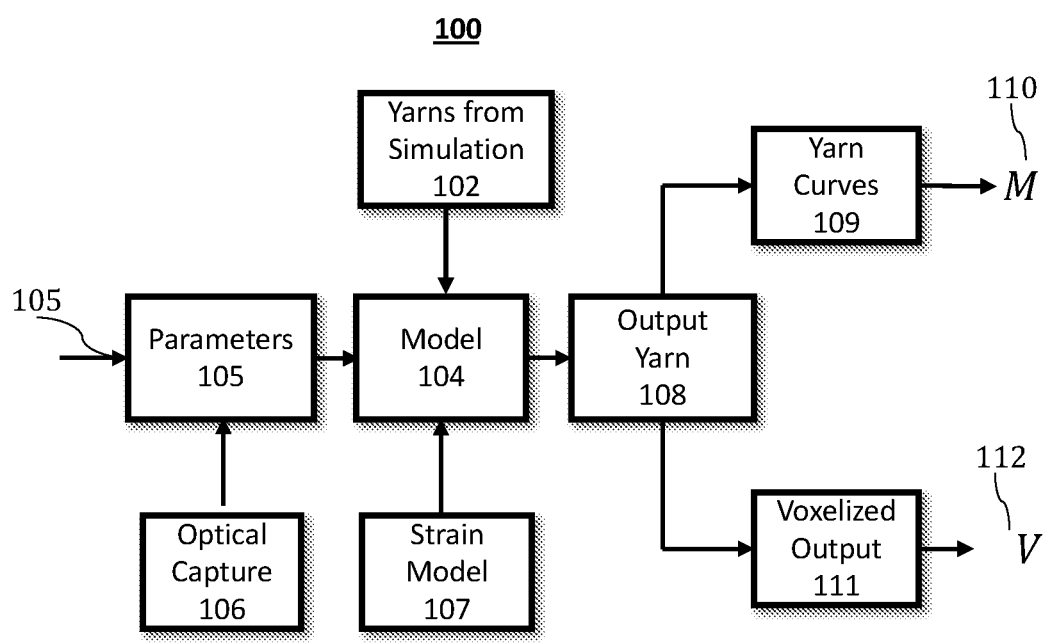
FIG. 1 illustrates a procedural model for fiber and yarn deformation according to one embodiment.

Now referring to FIG. 1, a modeling system and method is described according to one embodiment. A yarn is a group of plies with fibers that modify their positions along the distance of the yarn. The fibers can twist and turn together in each ply and around other plies along the yarn. Yarn simulations 102 provide a computer-based descriptive model of the general curvature followed by the yarn. The yarn simulations 102 are the basis of a model 104 according to various embodiments. In one embodiment, the model 104 includes the yarn simulation 102 augmented with a set of parameters 105 to define fibers and plies in the yarn defining a yarn cross-section. The parameters may be provided through user input 105a. In some examples, user input 105a may include parameters relating to user measurements or preferences, which may then be converted to a set of parameters 105 for input to model 104. Alternatively, the parameters may be based on an optical capture 106 (e.g., CT scans or other x-ray images of yarns, as well as other types of images or optical capture outputs), or from industry specifications (e.g., providing requirements such as number of fibers, fiber packing, yarn ellipticity through yarn twist, fiber radius through fiber type and/or material). In other embodiments, the parameters may be provided by other means as may be appropriate for the specific embodiment.

According to various embodiments, the parameters 105 may include number of plies, number of fibers per ply, ellipticity of plies, position of the center of the plies, fiber distribution in the cross-section, skewness of the fiber distribution, yarn twist, average, maximum, and minimum fiber lengths, and the like. The yarn model 104 is further augmented based on strain models 107. Strain models 107 provide the input for adapting the yarn model to applied forces, such as stretch, to produce a realistic yarn representation under different applied forces. For example, in a given garment worn by a modeled user, e.g., and avatar, the garment is subject to different stretch forces in different areas according to the underlying shapes in the body of the avatar. For example, stretch forces due to a shoulder's anatomical structure in a human avatar could cause some garments to stretch, being pulled down by the garment's own weight on both sides of the shoulder area. The model 104 is used to provide an output yarn 108 for each yarn subject to strain forces. As further described below, according to embodiments, the output yarn 108 provide a representation of the fibers making up the modeled yarn subject to the applied strain. For example, in one embodiment, the output yarn 108 includes a set or collection of modified or shifted fiber point samples. According to some embodiments, the point samples indicate a position and also provide information about the directionality of the fiber at each point based on, for example, a tangent direction. According to various embodiments, the output yarn 108 can then be processed using different approaches to generate images. For example, as illustrated in FIG. 1, in one embodiment, the output yarn 108 includes a set of points that are used to form yarn curves 109 to generate a graphical yarn model M 110. Alternatively, or in addition, in embodiments, the output yarn 108 is voxelized by a voxel output module 111 to provide a voxel-based output V 112, such as for example, a rasterized 3D grid, that can be rendered in a computer model. Other graphical representation of the output yarn 108 are possible in other embodiments and are within the scope of the invention.

Figure 2A:
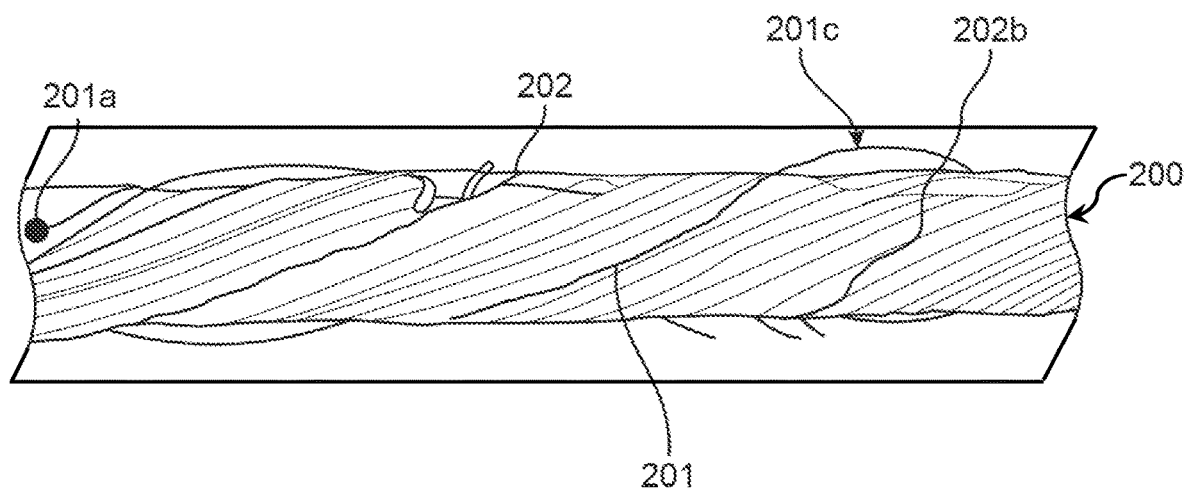
FIG. 2A is an illustrative diagram of an image of a yarn with fiber migration and fly-out according to one embodiment.

With reference to FIG. 2A, in one embodiment, two types of fiber effects are modeled: fiber migration and fiber fly-out. According to embodiments, a yarn 200 includes a plurality of fibers 201, 202, etc. Fiber migration, as for example illustrated by fiber 201, is the change of the position of a fiber along the yarn, which generally follows the direction of the yarn, with an additional distortion that depends on the level of twisting. Also, some of these fibers may randomly come out further from the center of the yarn, driven by the cross-section distribution. For example, fiber 201 starts at an initial position, 201a, and continues generally along the direction of the yarn 200 but includes a section that comes out further from the rest of the fibers at point 201c. Other fibers, such as for example fiber 202, can follow the direction of the yarn but at some point, the fly-out effect makes a change away from the main direction of the yarn, as illustrated by fiber 202 at point 202b, also illustrating how, in some cases, fibers can even break. According to one aspect of various embodiments, both types of effects are modeled without specific distinctions, as a continuum where the probability of a fiber to get out of the main group of fibers in the yarn is determined by a probability distribution function. The fiber length for each fiber has a pseudorandom value. In some embodiments, the fiber length is given by a pseudorandom value centered around an average length parameter, for example, a parameter for the given type of fiber. In addition, in one embodiment, a maximum and minimum deviation from the average length may also be a parameter characteristic of the type of fiber. In alternative embodiments, these parameters may be externally input, for example, as provided by a user. This approach better replicates the way real yarns are fabricated in the textile industry. For each fiber 201/202 in the model, the fiber direction and twist are computed based on applicable strain inputs.

Strain inputs are provided to the model, for example by a user or other modeling blocks in a larger modeling system. For example, in one embodiment, an avatar model may provide a strain input to the yarn model for the garments worn by the avatar. The strain inputs may, for example, be the result of the shapes underlying the fabric, external forces applied to the garment (e.g., pulling, compression, and the like), or other factors as may be desirable for a given modeled representation or scene. According to one embodiment, strain values are provided for each segment of yarn. A segment corresponds to each piece of yarn where a different strain value is computed by the simulation. The length of a segment is determined by the strain input to correspond to external forces causing the strain. The segments can be as short or long as may be necessary to model the stretching of the fabric or garment. For example, in one embodiment, segments may be placed between each pair of consecutive yarn crossings.

Figure 2B:
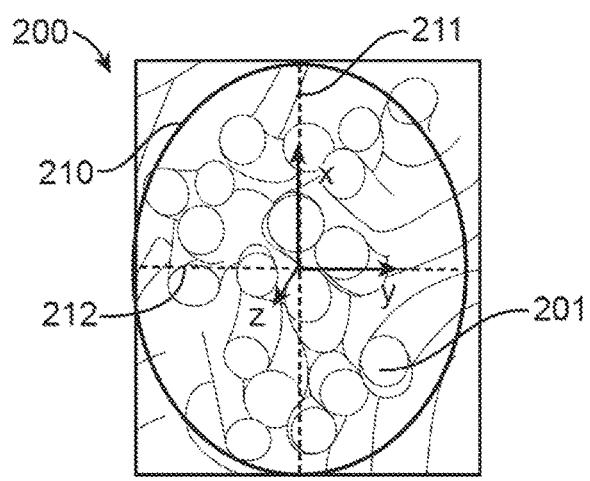
FIG. 2B is an illustrative diagram of a cross-section of a yarn according to one embodiment.

As depicted in FIG. 2B, in one embodiment, the yarn model 104 provides a procedural description of a yarn 200 modeled as a set of plies attached together. In each ply is further defined by a cross-sectional shape 210, for example, an ellipse, a circle, or the like. According to one aspect of embodiments of the invention, the shape is provided by a set of parameters that may be further constrained according to a strain model 107. In one embodiment, the strain model 107 provides a set of parameter modifications resulting from the computation of changes in the geometry of a stretched yarn model as a function of stretch. The stretch of the yarn causes changes to the yarn cross-section and orientation of the fibers 201 in the yarn.

According to one embodiment, the strain model 107 computes a change to the yarn geometry according to its cross-sectional shape. In this embodiment, the length of the stretched yarn segment l is the resulting length after the rest length $\bar{l}$ is stretched. When stretched, the length changes by an amount $\Delta l = l - \bar{l}$. In this embodiment, stretch is provided by a strain value $\varepsilon$:

$$\varepsilon = \frac{\Delta l}{l} \quad \text{[Eq. 1]}$$

In this embodiment, yarn twist is the twist angle of the fibers per unit length. The twist of the stretched yarn segment is $\omega$, and its rest twist is $\bar{\omega}$. According to some embodiments, the total twist angle of a yarn in the model remains constant when stretched. Yarn twist, however, may change, due to yarn stretch. In addition, as further depicted in FIG. 2B, a reference frame {x, y, z} is adapted to each yarn in the model, such that z is aligned with the yarn tangent, x is in the direction of the major axis 211 of the cross-section 210, and y is in the direction of the minor axis 212. According to one embodiment, the strain model 107 computes a change to the yarn geometry according to its elliptical cross-sectional shape.

The radius of the stretched yarn segment, when stretched, changes by a uniform amount. For yarns with elliptical cross-sections, the elliptical cross-section strain is assumed to be the same for the major and minor axes. At rest, when not stretched, the rest lengths of the semi-axes are $\bar{a}$ and $\bar{b}$ respectively. When the yarn is stretched, the lengths of the semi-axes change by the amounts $\Delta a = a - \bar{a}$ and $\Delta b = b - \bar{b}$. Assume both axes undergo the same strain, the cross-section strain is $$\lambda = \frac{\Delta a}{a} = \frac{\Delta b}{b}.$$

Further, given the rest volume of a yarn segment, $V = \bar{l}\pi\bar{a}\bar{b}$, the volume V of the stretched yarn segment with elliptical cross-section can be expressed as a function of yarn stretch E and the change of length of the semi-axes according to Equation 2:

$$V = (1+\varepsilon)\bar{l}\pi(1+\lambda)^2 \overline{ab} \quad \text{[Eq. 2]}$$

The cross-section strain $\lambda$ defines the relative change of radius, which is considered the same for the major and minor axes of the ellipse. As a result of volume conservation, the cross-section strain $\lambda$ is given by Equation 3:

$$\lambda = \frac{1}{\sqrt{1+\varepsilon}} - 1 \quad \text{[Eq. 3]}$$

For a yarn with multiple consecutive segments, the cross-section strain may be interpolated to obtain smooth visual results.

In another embodiment we can further account for fiber packing through a parameter $\alpha$, by multiplying the expression of $\lambda$ in Equation 3 by the coefficient $\alpha$.

According to this embodiment, fibers 201/202 are initialized with an angular and a radial position on the cross-section plane. The initial angular position is computed using a uniform probability distribution. The initial radial position is determined with a pseudorandom function that gives the position of a fiber in a point over the cross-section of a yarn. In one embodiment, the Cauchy probability density function is used according to Equation 4:

$$f(R; R_0, \gamma) = \frac{1}{\pi\gamma\left[1 + \left(\frac{R - R_0}{\gamma}\right)^2\right]} \quad \text{[Eq. 4]}$$

Where $R_0$ is the location parameter, specifying the radial location of the peak of the distribution of fibers in the cross-section of a yarn, and $\gamma$ is the scale parameter which specifies the half-width at half-maximum.

According to various embodiments, fiber migration and fly-out effects are modeled separately for each fiber, for example, in one embodiment, a pseudorandom function is used to model each effect for every fiber. Once the migration and fly-out effects are independently computed, they are applied to the fiber position function. For example, in one embodiment, the two pseudorandom functions are parametrically weighted and composed together. In one embodiment, the weights applied to the migration and fly-out effects are correlated, for example, adding to an integer value such as 1, 100, or the like. In alternative embodiments the weights applied to the migration and fly-out effects may be unrelated and separately affect the impact of each of the two effects on each fiber. The procedural model according to this embodiment is constrained by restricting movement of the fibers by the probability of being out of the center. As a result, fibers close to the border of the yarn are more likely to migrate more distance than the fibers close to the center of the yarn.

Figure 3:
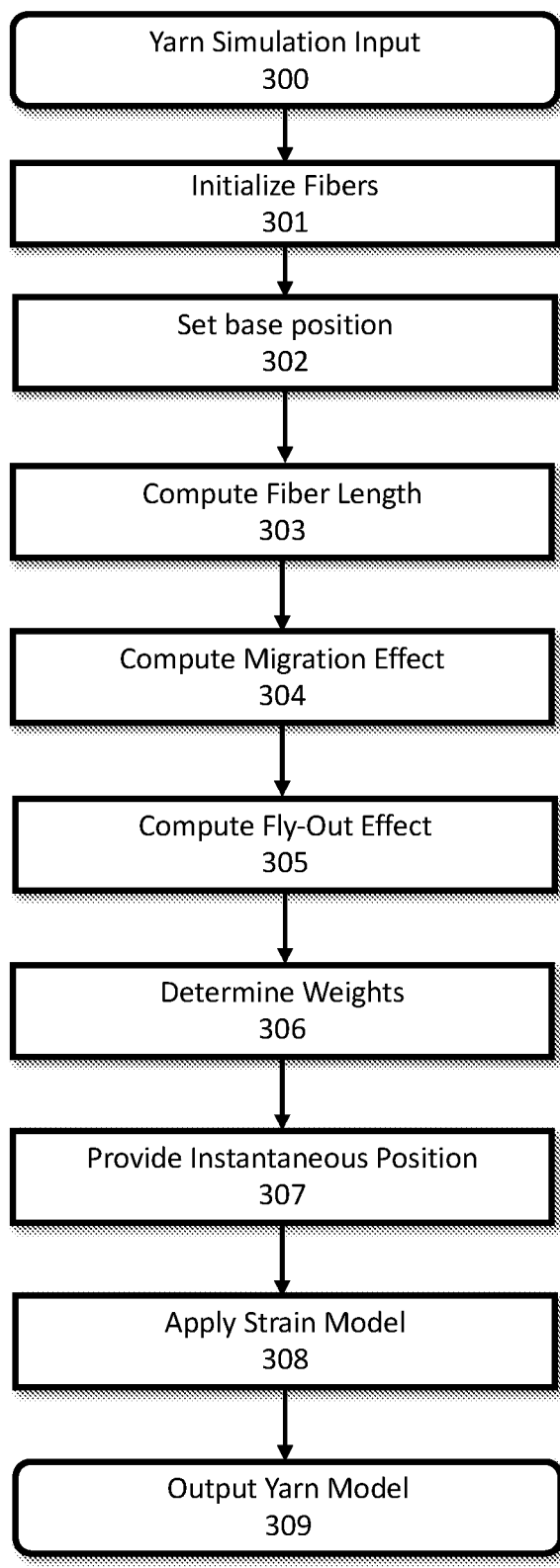
FIG. 3 is a flow chart for a yarn modeling method according to one embodiment.

Now referring to FIG. 3, in one embodiment, the initial yarn simulation input 300 is received. At the initial position of the yarn, e.g., length of zero, the yarn is initialized (i.e., started) 301 with a number of fibers distributed radially from the ply's center. Each fiber is randomly distributed following a probability distribution function, such as for example, a Cauchy distribution. During initialization 301, the parameter values received as input are applied to the initial yarn and fiber model. For example, the selected number of plies, the number of fibers per ply, and the cross-sectional shape selection are applied to the initial fiber models, which comprise initial point samples indicating a position and directionality of the fiber at each point. Based on the parametric input, the center of the plies is computed and the initial fiber distribution is computed using the probability density function as described above.

In one embodiment, a Cauchy distribution is used to radially sample fibers using the analytic quantile Q, the inverse of the cumulative distribution function:

$$Q(F; R_0, \gamma) = R_0 + \gamma \tan\left[\pi\left(F - \frac{1}{2}\right)\right] \quad \text{[Eq. 5]}$$

According to another aspect of various embodiments, the distribution of the fibers in the ply cross-section may also present skewness, depending on the arrangement of the plies making up the yarn.

According to various embodiments, once the fibers in the yarn model are initialized 301, at any location along the length of the yarn, a base position for each fiber is defined 302 as $p_0$, as for example illustrated in FIG. 2A as base position 201a for fiber 201. In one embodiment, the base position is computed based on a set of parameters. For example, the base position may be computed based on the position of the fiber at initialization, the current location along the length of the yarn, the center line of the yarn in 3D, and the twist of the yarn, among other possible parameters. In one embodiment, the twist of the yarn determines how the fiber moves on the yarn cross-section as the length of the yarn is traversed, while the cross-section of the yarn is translated and rotated in 3D along the center line of the yarn.

In addition, in various embodiments, for each fiber, a fiber length parameter is defined 303 using a pseudorandom function. In some embodiments, the fiber length is given by a pseudorandom value centered around an average length parameter, for example, a parameter for the given type of fiber. In addition, in one embodiment, a maximum and minimum deviation from the average length may also be a parameter characteristic of the type of fiber. Once a fiber reaches the end of its length, the fiber length value is resampled. The pseudorandom lengths of the fibers according to embodiments of the fiber model described herein more realistically represent real yarns and avoid visually apparent periodic patterns.

According to various embodiments, for each fiber, a maximum migration and fly-out displacements are computed 304/305. For example, in one embodiment, the three-dimensional displacements of fiber migration, $p_m$, and fiber fly-out, $p_f$, are defined as weighted sums of a varying number of analytic periodic functions of different amplitudes and frequencies and are given by pseudo-random functions, prm and prf, such as, for example, three-dimensional Perlin Noise functions (see Perlin, Ken (July 1985) "*An Image Synthesizer*," SIGGRAPH Comput. Graph. 19 (0097-8930): 287-296, incorporated herein by reference) with pseudo-random sequences that are added increasing their frequency (F) and decreasing their amplitude (A). Each random function is defined by the current distance of the fiber (x,y,z) and input seeds M and F as follows:

$$p_m(t) = [prm(x, M_1, Am_x, Fm), prm(y, M_2, Am_y, Fm), 0]$$

$$p_f(t) = [prf(x, F_1, Af_x, Ff), prf(y, F_2, Af_y, Ff),), prf(z, F_3, Af_3, Ff)]$$

Further, for each fiber, and at every location along the length of the yarn, pseudorandom weights applicable to the migration, $p_m$, and fiber fly-out, $p_f$ displacements are determined 306. In one embodiment, these weights are determined as a function of the distance to the fiber endings and the distance to the center of the ply. For example, a higher weight of the migration displacement may be assigned to fiber points further from the fiber endings, and a higher weight of the fly-out displacement may be assigned to fiber points closer to the fiber endings. In addition, in some embodiments, both weights may be modified in a pseudo-random manner based the density of fibers in the cross-section of the ply. In some embodiments, this density may be modeled using a Cauchy probability distribution as a function of the distance to the center of the ply.

With migration displacement $p_m$, fly-out displacement $p_f$, migration weight $w_m$, and fly-out weight $w_f$, the position of the fiber is redefined from the base position $p_0$, as:

$$\bar{p}(t) = p_0 + w_m(t) * p_m(t) w_f(t) * p_f(t) \quad \text{[Eq. 6]}$$

Finally, according to some embodiments, the strain model is applied 308 to modify the position of each fiber on the cross-section, according to the instantaneous strain of the yarn. With the three-dimensional "at rest" point having been determined for a given fiber, its position in the cross-section of the fiber at that location is given as $\bar{p} = (\bar{x}, \bar{y}, \bar{z})^T$. The effects of strain can be applied by determining its deformed position, $p = (x, y, z)^T$, with $p = ((1+\lambda)\bar{x}, (1+\lambda)\bar{y}, \bar{z})^T$, and then obtain the tangent and direction (i.e., deformed tangent vector) of the fiber at that point due to the applied stretch $\varepsilon$.

Given the assumption that the twist angle of a yarn segment remains constant upon the application of stretch, $\varepsilon$ in Eq. 1, the twist $\omega$ varies with stretch as follows:

$$\omega = \frac{\bar{\omega}}{1 + \varepsilon} \quad \text{[Eq. 7]}$$

To derive the tangent u of the fiber passing through point $p = (x, y, z)^T$, a distance dz is stepped along the tangent of the yarn. Given the twist angle that the cross-section undergoes with stretch, $d\theta = \omega dz$, the tangent vector u is given by the following:

$$u = \frac{1}{\sqrt{1+\omega^2 x^2 + \omega^2 y^2}} \cdot \begin{pmatrix} -\omega y \\ \omega x \\ 1 \end{pmatrix} \qquad \text{[Eq. 8]}$$

Given u, the location and direction of each of the fibers in the yarn can be determined and the output yarn model can be computed 309 for output.

According to embodiments, the procedural output yarn model provides a representation of the fibers making up the modeled yarn subject to the applied strain. For example, in one embodiment, the output yarn model includes a set or collection of fiber point samples, some or all of which may be modified or shifted from their initial position and direction (i.e., such that the output yarn model includes some shifted point samples). According to some embodiments, the shifted point samples indicate a position and also provide information about the directionality of the fiber at each point based on, for example, a tangent direction. According to various embodiments, the yarn output model is further processed using different approaches to generate images. For example, in one embodiment, the output yarn model includes a set of points that are used to form yarn curves to generate a graphical yarn model M. Alternatively, or in addition, in embodiments, the output yarn model is voxelized to provide a voxel-based output V.

For example, according to one embodiment, the data of the procedural yarn model is stored in a 3D grid for use in producing the final images according to the model. According to one embodiment, the occupation of each cube or voxel is determined and stored in the voxel grid. The occupation per voxel is the relationship between the volume occupied by the fibers of the yarn and the total volume of the voxel. Depending on the voxelization algorithm, the occupation may be computed based on fragments or samples generated by a rasterization process. In an example, the occupation is computed by extruding an area associated with the sample. In another example, the occupation is computed through a virtual subgrid. A procedural cylinder may be also used to model the fiber and produce fragments over the surface of the cylinder. The total volume of the cylinder is the integration of every fragment extruded from the fragment position to the center of the fiber. The result of the volume integration divided by the volume of a voxel, gives us the percentage of a voxel occupation. Other graphics-based processing of the procedural output yarn model are possible in other embodiments and are within the scope of the invention.

According to one embodiment, the yarn model can be further integrated with thread-level behavioral models of textiles to increase photo-realistic look of the model. For example, as described in EP 3 223 176 A1. According to this embodiment, the yarn model is additionally subjected to yarn-level mechanics to enhance the model with the discretization of yarn kinematics based on the positions of yarn crossing points and yarn sliding.

According to other embodiments, the above-described real-time modeling techniques can be used in a wide range of computer graphics and simulation applications, like video games, animated films, virtual or augmented reality applications, garment design, garment fitting, and the like.

The foregoing description of the embodiments has been presented for the purpose of illustration; it is not intended to be exhaustive or to limit the patent rights to the precise forms disclosed. Persons skilled in the relevant art can appreciate that many modifications and variations are possible in light of the above disclosure.

Some portions of this description describe the embodiments in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Any of the steps, operations, or processes described herein may be performed or implemented with one or more hardware or software modules, alone or in combination with other devices. In one embodiment, a software module is implemented with a computer program product comprising a computer-readable medium containing computer program code, which can be executed by a computer processor for performing any or all of the steps, operations, or processes described.

Embodiments may also relate to an apparatus for performing the operations herein. This apparatus may be specially constructed for the required purposes, and/or it may comprise a general-purpose computing device selectively activated or reconfigured by a computer program stored in the computer. Such a computer program may be stored in a non-transitory, tangible computer readable storage medium, or any type of media suitable for storing electronic instructions, which may be coupled to a computer system bus. Furthermore, any computing systems referred to in the specification may include a single processor or may be architectures employing multiple processor designs for increased computing capability.

Finally, the language used in the specification has been principally selected for readability and instructional purposes, and it may not have been selected to delineate or circumscribe the inventive subject matter. It is therefore intended that the scope of the patent rights be limited not by this detailed description, but rather by any claims that issue on an application based hereon. Accordingly, the disclosure of the embodiments is intended to be illustrative, but not limiting, of the scope of the patent rights, which is set forth in the following.

What is claimed is:

1. A computer implemented method for generating a model of a yarn, the method comprising:
   receiving a yarn simulation input comprising a descriptive model of a general curvature followed by a simulated yarn;
   providing, at an initial position of the simulated yarn comprising at least one ply, a plurality of simulated fibers distributed radially from the at least one ply's center, the simulated fibers comprising a plurality of point samples, each point sample indicating a position and directionality of one of the plurality of simulated fibers at each point along the simulated yarn;
   determining an end position of each of the plurality of simulated fibers, wherein the end position of each of the plurality of simulated fibers is defined by a distance from the center of the fiber to the at least one ply's center calculated using a random function according to a Cauchy distribution function;

applying a strain model to the simulated yarn, the strain model configured to simulate an effect of stretch forces applied to the simulated yarn; and outputting a yarn cross-section model comprising at least one shifted point sample.

2. The method of claim 1, wherein providing the plurality of simulated fibers comprises initializing a description for each of the plurality of simulated fibers with an initial angular position and an initial radial position on a simulated cross-section plane corresponding to the cross-section of the simulated yarn.

3. The method of claim 2, wherein the initial angular position is computed using a uniform probability distribution.

4. The method of claim 2, wherein the initial radial position is computed using a pseudorandom function.

5. The method of claim 1, wherein applying the strain model comprises determining a deformed position for each of the plurality of simulated fibers.

6. The method of claim 1, wherein applying the strain model comprises determining a deformed tangent vector for each of the plurality of simulated fibers.

7. The method of claim 1, wherein the end position of each of the plurality of simulated fibers further is defined by a two-dimensional position calculated using a uniform random function.

8. The method of claim 1, further comprising receiving a parameter input.

9. The method of claim 8, wherein the parameter input comprises an optical input.

10. The method of claim 9, wherein the optical input comprises a computed tomography scan.

11. The method of claim 8, wherein the parameter input comprises an image.

12. The method of claim 1, further comprising generating an image using the yarn model.

13. The method of claim 1, further comprising generating a voxel-based output using the yarn model.

14. The method of claim 1, further comprising computing a fiber migration displacement for each of the plurality of simulated fibers using a pseudorandom weight.

15. The method of claim 1, further comprising computing a fiber fly-out effect for each of the plurality of simulated fibers using a pseudorandom weight.

\* \* \* \* \*